United States Patent

Whang

[11] Patent Number: 5,914,130
[45] Date of Patent: *Jun. 22, 1999

[54] POTASSIUM AND SODIUM BICARBONATE FOR INCREASED BLOOD BUFFERS

[75] Inventor: Sang Youn Whang, Miami, Fla.

[73] Assignee: Sang Whang Enterprises, Inc., Miami, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/560,935

[22] Filed: Nov. 20, 1995

[51] Int. Cl.$^6$ ...................................................... A61K 9/20
[52] U.S. Cl. ............................ 424/466; 424/464; 424/465
[58] Field of Search ..................................... 424/464, 465, 424/466

[56] References Cited

U.S. PATENT DOCUMENTS

| | | | |
|---|---|---|---|
| 4,725,427 | 2/1988 | Ashmead et al. | 424/44 |
| 4,752,479 | 6/1988 | Briggs et al. | 424/472 |
| 5,306,511 | 4/1994 | Whang | 426/66 |

*Primary Examiner*—Jos' G. Dees
*Assistant Examiner*—Kathryne E. Shelborne

[57] ABSTRACT

A human consumable chemical compound of specific selected ranges of potassium bicarbonate and sodium bicarbonate is provided. A potassium predominant bicarbonate mixture in tablet form is a substitute for alkaline drinking water. The lung's exhaling of carbon dioxide provides a required mechanism for activating this chemical compound to become alkaline. Balanced chemical supply of potassium bicarbonate and sodium bicarbonate neutralizes the body's harmful acidic wastes and is beneficial to one's health.

9 Claims, No Drawings

POTASSIUM AND SODIUM BICARBONATE FOR INCREASED BLOOD BUFFERS

FIELD OF THE INVENTION

The field of the present invention relates broadly to methods and compounds pertaining to health. More specifically, the invention relates to a human consumable chemical compound of specific selected ranges of potassium bicarbonate and sodium bicarbonate. Such a compound, in oral, time-release form supplies all the daily requirements for neutralizing acidic body wastes for that particular time release period.

Still more particularly, the invention pertains to a chemical compound that persons may take as a substitute source for alkaline drinking water. Such a compound, in pill form, is a convenient, readily consumable substitute source for healthy alkaline drinking water.

DESCRIPTION OF PRIOR ART

New medical developments, devices and health aids are emerging on the domestic market at an ever increasing pace. The benefits, for example of alkaline water and related devices relevant to its commercialization are well set forth in my issued U.S. Pat. No. 5,306,511 and need not be repeated here. Briefly, however, my patent sets forth the basis for the unquestioned advantages of alkaline water in general—whether such water is ionizer-machine-produced or additive produced.

Alkaline drinking water of increased oxygen has a pH in the range of about 8.5 to about 10.5. AlkaLife® of my '511 patent is a readily available source of alkaline water. Such water is made by simply adding a couple of drops of my patented additive to a 10 ounce glass of water in order to make the pH of the water about 10.

An increasingly large segment of the consuming public is now relying on alkaline water, particularly my additive-produced alkaline water. Experience indicates that a person should drink five glasses of alkaline water a day in order to get the health benefits of reduced acid in the body. Body-created acids are neutralized by alkaline water, so that they may easily be discharged from the body by urine and perspiration.

Since the body's acid waste products are produced continuously throughout the day, one should drink five glasses of alkaline water, not all at once, but more or less evenly distributed throughout the day. In practice, however, it is not easy to do so—day in, and day out. In our busy life, it seems, we even skip meals, never mind drinking five evenly spaced glasses of alkaline water throughout the day.

Individual pills of potassium bicarbonate or sodium bicarbonate alone are available in the art. Doctors Anthony Sebastian et al in the New England Journal of Medicine, Jun. 23, 1994, report this practice in an article entitled: "Improved mineral balance and skeletal metabolism in post-menopausal women treated with potassium bicarbonate".

It is also known to prescribe sodium bicarbonate pills prior to chemotherapy. Cells that are killed by chemotherapy become acid waste in our bodies.

It is also common to take vitamins that include small amounts of sodium, potassium and other minerals. Such vitamin-supplied minerals are an attempt to meet our daily needs for these required substances. There is no attempt to use such vitamin minerals for purposes of neutralizing acidic body waste, nor to act as an alkaline water substitute.

Moreover, there are various indigestion salts and commercial remedies—such as Alka Seltzer and Alka Seltzer Effervescent Antiacid—that are available in the art. Such indigestion remedies primarily are designed for pre-mixture in water and subsequent human consumption. Products such as these contain sodium bicarbonate, citric acid, aspirin and to a lesser extent even potassium bicarbonate.

In general, however, such indigestion mixtures do not contain potassium bicarbonate at all. Or, if some potassium bicarbonate is present, the amount is small in comparison to a predominantly larger percentage of sodium bicarbonate. Products of this type, therefore, are going in a wrong direction and teach away from the scope, power and novelty of this invention.

How does one achieve the benefits of drinking alkaline water without suffering from a rigid water consumption schedule? That is the purpose of this invention. In other words, what had not been solved before the advent of this invention was a simple, effective chemical compound that achieves the benefits of alkaline water without the necessity of drinking five or more time-spaced glasses of such water per day.

This invention creates a new compound—perhaps in a pill form—that one can take once a day in the morning; which compound will provide the same effect as drinking five glasses of alkaline water a day distributed throughout the day. Thus, a person relying on the invention is relieved of the strict, rigid time schedule demand of drinking spaced glasses of alkaline water. One's overall health benefits from use of the invention, and one is relieved from some of the pressures caused by today's busy and hectic work-a-day fast paced life.

SUMMARY OF THE INVENTION

This invention provides a human consumable chemical compound of specific selected ranges of potassium bicarbonate and sodium bicarbonate for the purpose of neutralizing body acid waste. More particularly, the invention combines such bicarbonate mixture in a pill form as a substitute for alkaline drinking water. The invented compound of this invention shall be commercialized and sold by the assignee of this invention under the selected tradename of AlkaMin™.

This invention is further characterized by relying on the lung's exhaling ability of carbon dioxide to provide the required mechanism for activating my novel compound. The bodies natural adaptation to intake, together with a balanced chemical supply of potassium bicarbonate and sodium bicarbonate, is employed to neutralize the body's harmful acidic wastes and promote an easy removal of such neutralized body waste.

In using this invention, a person's blood pH remains at a safe and stable value and the health is improved. In time release form the invention provides both convenience and a natural dissolving process in the body. Thus, my orally consumable chemical compound invention readily and conveniently becomes a safe substitute for achieving all of the beneficial effects of alkaline water in the body of the user.

Packaged chemical inventive compounds—in time release pill form—become a ready one-a-day substitute which achieves the same acid reduction capability in the body that drinking five equally spaced, ten ounce glasses per day of alkaline drinking water achieves. Beneficial health results are thus achieved by a novel compound mixture and method of relying on the lung's natural body functioning in order to activate a novel chemical formula within a user's body.

OBJECTS OF THE INVENTION

It is an object of the present invention to provide a convenient chemical source as a human consumable substitute for alkaline drinking water.

It is another object of my invention to prepare an alkaline drinking water substitute by use of safe neutral compounds of potassium bicarbonates and sodium bicarbonates which are made alkaline within the user's body by natural body functions.

It is still another object of this invention to formulate an alkaline drinking water substitute from safe neutral bicarbonates of potassium and sodium in a mixture having specific percentage ranges of these ingredients.

It is yet another object of this invention to neutralize and reduce the body's acidic waste products by a readily consumable chemical in pill form—perhaps of the time release pill variety.

It is still a further object of this invention to provide in a chemical or pill form, safe neutral compounds of $KHCO_3$ (potassium bicarbonate) and $NaHCO_3$ (sodium bicarbonate) in order to produce the equivalent effects of drinking alkaline water.

It is still a further object of this invention to provide a pill-supplied source of potassium bicarbonate ($KHCO_3$) and sodium bicarbonate ($NaHCO_3$) in an orally administered time release pill.

It is still a further object of this invention to prevent increased body acidity through blood buffers such as a mixture of weak acids and salts of strong bases.

One additional object is to allow an orally administered blood buffer to keep the body's pH value from experiencing extreme fluctuations.

It is still one further object of this invention to provide and maintain the proper ratio of potassium and sodium in the human body over prolonged periods of time.

Another object is to increase sodium bicarbonate in the blood while also increasing the amount of potassium absorbed in the human body cells.

It is yet one further object of this invention to provide a time release pill compound of bicarbonates selected at the ratio of about 75% (potassium bicarbonate) to about 25% (sodium bicarbonate) as the primary ingredients for an alkaline drinking water substitute.

DESCRIPTION OF PREFERRED EXAMPLE EMBODIMENT AND BEST MODE OF THE INVENTION

Turning now to a detailed description of the invention, which may be understood without reference to any drawing, one must first briefly understand the human aging process. Aging is primarily marked by the accumulation of non-disposed acidic waste products that our cells produce as they burn nutrients to generate energy. We need to burn nutrients in order to function and live.

Acid coagulates blood and the accumulated acidic wastes of our bodies clog our capillary vessels and reduce blood circulation near the accumulated waste locations. It is believed that this phenomena is the primary cause of adult diseases such as diabetes, kidney disease, and the like.

It is also believed important for an understanding of the invention, to note the effects of alkaline water in the human body. Drinking alkaline water neutralizes and reduces the acidic waste products created within our bodies. Thus, people drinking alkaline water have observed many health improvements over the years. In accordance with this invention, the alkaline water benefits are available in readily consumable chemical pill, tablet or caplet form.

Acid substance when dissolved in water causes the water to have more hydrogen ions ($H^+$) than hydroxyl ions ($OH^-$). Alkaline water contains more hydroxyl ions ($OH^-$) than hydrogen ions ($H^+$). Neutralizing acid with alkaline means supplying hydroxyl ions ($OH^-$) so that the excess $H^+$ ions in acid will become $H_2O$ or water by combining with $OH^-$ ions.

$$H^+ + OH^- = H_2O$$

There are approximately $1 \times 10^{25}$ number of $H_2O$ water molecules in a 10 oz. glass of water. The pH value of 10 means that there are $1 \times 10^{21}$ number of hydroxyl ions ($OH^-$) in that 10 oz glass of water. Assuming that 70% of the $OH^-$ ions are mated with potassium ions ($K^+$) and 30% of the $OH^-$ ions are mated with sodium ions ($Na^+$), then one may compute the respective number of KOH molecules and NaOH molecules as $7 \times 10^{20}$ and $3 \times 10^{20}$.

From the molecular weights of these materials, it can be calculated that in a 10 oz glass of (pH 10) alkaline water made by AlkaLife® there are 65.1 mg of KOH and 19.9 mg of NaOH.

Since KOH and NaOH are caustic, taking 65.1 mg of KOH and 19.9 mg of NaOH in a pill form is poisonous. For this reason, AlkaLife® of my '511 patent is already diluted in $H_2O$, and two drops of AlkaLife® is added (further diluted) to a 10 oz glass of drinking water in order to make it an alkaline water with the pH value of about 10. In a liquid form this packaging and dilution process is possible.

In a chemical or pill form, I am proposing safe neutral compounds of $KHCO_3$ (potassium bicarbonate) and $NaHCO_3$ (sodium bicarbonate). In order to produce the equivalent effect of 10 oz. alkaline water, there must be 116.2 mg of $KHCO_3$ and 41.8 mg of $NaHCO_3$. For fifty (50) ounces of alkaline water (one day's drinking water amount), there must be 581.2 mg of $KHCO_3$ and 209.2 mg of $NaHCO_3$. If these amounts of potassium bicarbonate ($KHCO_3$) and sodium bicarbonate ($NaHCO_3$) are put in a time release pill form, taking such a pill once a day in the morning will provide the effect of drinking five well spaced glasses of alkaline water a day.

The human blood is slightly alkaline and its pH value must be maintained between 7.3 and 7.4. Even minor variations are dangerous. If the blood pH value drops to 6.95 (barley over the line on the acid side), coma and death results. And, if the blood pH value rises to 7.5 to 7.7, titanic convulsions occur. With acid blood, the heart relaxes and ceases to beat, and with too alkaline blood it contracts and ceases to beat. [Acid & Alkaline by Herman Aihara, George Ohsawa Macrobiotic Foundation, 1986]

In the human blood plasma, two compounds are dissolved. One is sodium bicarbonate ($NaHCO_3$) (alkaline buffer) and the other is carbonic acid ($H_2CO_3$) (volatile acid). If we increase the amount of carbonic acid, as by exercise, the blood becomes more acid.

As we all know, we breath out carbon dioxide $CO_2$ constantly. That means the volatile acid $H_2CO_3$ in the blood loses $CO_2$ easily and becomes $H_2O$. Thus the blood becomes less acid or more alkaline. As our blood gets more acidic—or builds up more carbonic acid—we exhale more $CO_2$ to maintain a stable and safe level alkalinity for our blood.

Another way the body prevents increased acidity is through blood buffers such as sodium bicarbonate ($NaHCO_3$). Blood buffers are mixtures of weak acids and salts of strong bases. Blood buffers work to keep the pH value from experiencing extreme fluctuations, and thus resist changes in hydrogen ion concentration.

If a strong acid, such as hydrochloric acid, sulfuric acid, or lactic acid, which we may symbolize as HX, is added to the blood, it unites with some of the sodium of the sodium bicarbonate and drives off carbon dioxide, according to the following equation:

$$HX + NaHCO_3 = NaX + H_2O + CO_2 = NaX + H_2CO_3$$

Addition of a strong acid, HX, to the blood results in an alkaline or neutral substance NaX plus carbonic acid, $H_2CO_3$, which is a volatile weak acid that can easily be transformed into water by lung exhalation of $CO_2$. Another way to look at it, is that the lungs remove $CO_2$ from sodium bicarbonate, $NaHCO_3$, thus leaving sodium hydroxide, NaOH. Sodium hydroxide is strongly alkaline and thus sodium hydroxide, NaOH will neutralize this strong acid HX.

$$NaHCO_3 - CO_2 = NaOH$$

$$NaOH + HX = NaX + H_2O$$

Potassium bicarbonate can act as buffer also. However, in the human body, potassium is more in the cells while sodium is more in the extra cellular fluids and the blood. It is very important to maintain the proper ratio of potassium and sodium in the human body. If you want to increase sodium bicarbonate in the blood, you must increase the potassium in the body as well.

Individual pills of potassium bicarbonate and sodium bicarbonate are available already. Doctors Anthony Sebastian et al in the New England Journal of Medicine, Jun. 23, 1994 reported as such in the article entitled "Improved mineral balance and skeletal metabolism in postmenopausal women treated with potassium bicarbonate". I also know a doctor who prescribes sodium bicarbonate pills (600 mgs, 4 times a day) prior to chemotherapy to raise the urine pH value to 7.5, alkaline urine. This prescription approach is to reduce the side effects that could be caused by the generation of acid wastes when chemotherapy is administered.

Doctors do not prescribe these pills too long, longer than necessary to see the desired effects, because the prolonged consumption of high doses of these chemical can create an imbalance of potassium and sodium mineral contents in the human body. This imbalance can cause many bad side effects. For instance, potassium deficient diet or too much sodium intake can cause loss of potassium in the urine. This, in turn, may cause a water retention problem that increases the volume of blood and can cause high blood pressure.

The pill that I am teaching in this invention, has a proper balance of potassium and sodium, and yet meets the amount of our relatively low daily needs for potassium and sodium. The amount of potassium minerals in 581.2 mg of $KHCO_3$ is 226.7 mg and the amount of sodium minerals in 209.2 mg of $NaHCO_3$ is 57.3 mg. These amounts are well below the minimum daily requirements of these minerals.

To pick a more familiar example, just to give one an idea of the magnitude of mineral intake, one cup of unseasoned soybeans contains about 1080 mg of potassium and one cup of macaroni baked with cheese contains about 1,192 mg of sodium. That being the case, one might ask can't eating soybeans and macaroni with cheese do a better job than drinking alkaline water or taking this new chemical pill invention?

My answer is: It's not the amount of minerals that's important, but what those minerals are mated with that is significant. In alkaline water and/or my pill invention, those minerals are mated with hydroxyl ions ($OH^-$) which neutralize acid hydrogen ions ($H^+$) in the waste that human cells make. As explained hereinafter such mating is critical.

When one drinks high pH alkaline water, the human stomach wall secrets hydrochloric acid (HCl) to maintain the stomach pH value to acid level of 4. The stomach wall cells produce hydrochloric acid from three molecules, namely salt (NaCl or KCl), water ($H_2O$) and carbon dioxide ($CO_2$). The leftovers are the bicarbonates that goes into the blood.

$$NaCl + H_2O + CO_2 = HCl + NaHCO_3 \text{ or}$$

$$KCl + H_2O + CO_2 = HCl + KHCO_3$$

The more alkaline water one drinks, the more hydrochloric acid is secreted and thus more bicarbonates go into the blood. The new pill (AlkaMin™) is already in the form of potassium and sodium bicarbonate which is neutral but can be converted into alkaline as needed by exhaling carbon dioxide by the lungs.

As these bicarbonates are used to neutralize acid wastes, more carbonic acid ($H_2CO_3$) is created, and it in turn forces the lungs to exhale more $CO_2$ in order to maintain our blood pH at a safe and stable value. People with acidosis problems, for example, are the ones with not enough bicarbonates.

Calcium carbonates and magnesium carbonates are available in the form of vitamins; however, they do not dissolve well and thus are not sufficiently effective to function as acid neutralizing alkaline solutions. Moreover the function and purpose of such vitamins is different than those of this invention.

Additional inert compounds to make a pill a slow time release pill, or additional coating material that spreads out the pill's dissolution time, of course, are well known in the art. In the relevant art these slow acting pills have been described by various terms such as extended release, sustained release, controlled release, delayed release, sustained action, continuous action and slow release. All of these terms mean essentially the same thing—namely, that the action of the pill is spread out over an extended period of time.

Pills that are coated for a slow time release are referred to in the art as Enteric Coated Tablets. Another approach that is well known, for example, is to place the chemical compound in a cellulosic binder that decomposes over a period of several hours in the stomach or intestine environment. Such known and well recognized techniques may be utilized to achieve a time release capability for the potassium predominant compound of my invention. Although such time release factors are of importance to my concept they are not a critical feature of this invention.

What is important, however, is the combination of potassium and sodium bicarbonate—perhaps in a time release form. In the specific example for this invention, the percentage of potassium bicarbonate is 73.5% while that of sodium bicarbonate is 26.5%. The specific inventive range should be from about 95% to about 50% potassium in comparison, respectively, to about 5% to about 50% of sodium.

In this specification I have referred to these range values as being a potassium predominant mixture, in order to distinguish my teaching from the known art. As noted earlier, the art has primarily taught compound mixtures formed in the opposite direction wherein sodium is, by far, the highest percentage ingredient.

The alkaline water substitute of this invention is not a medicine to treat or cure any disease. It does, however, neutralize excess body acids and helps the body dispose of such neutralized body acids. By so doing, the health of many people has improved in a natural way which is enhanced by alkaline drinking water.

What I am focussing on in the preferred embodiment is that percentage which, on balance, will give the best result for each particular individual. Skin Resistance Measuring ("SRM") devices as discussed in my '511 patent, are available for tailoring substances to each individual's needs. In the future when such SRM instruments become more readily available, optimum individualized chemical compounds may be tailor-made as individualized one-a-day time release pills. Such compound pills however, should nevertheless be formulated from 95% to about 50% potassium bicarbonate to about 5% to 50% percent sodium bicarbonate in accordance with the principles of this invention for best results.

Until such individualized tailor-made SRM chemical compounds are available on a widespread basis, however, a time release pill combination of about 75% (potassium bicarbonate) to about 25% (sodium bicarbonate) for the primary ingredients will be used as an alkaline drinking water substitute.

It should also be understood, of course, that one could also add a small amount of other alkaline and inert time release minerals to the chemical compound of this invention. However, the ratio of potassium bicarbonate to sodium bicarbonate should still be maintained within the general potassium predominant ranges set forth in this specification and claims.

While my invention has been described with reference to a particular example of preferred embodiments, it is my intention to cover all modifications and equivalents within the scope of the following appended claims. It is therefore requested that the following claims be given a liberal interpretation which is within the spirit and scope of my contribution to this art.

What is claimed is:

1. A non caustic, swallowable pill for conversion into an alkaline blood buffer in the body to reduce body acid including hydrogen ions ($H^+$) and to act as a long term substitute for drinking daily amounts of alkaline water, said substitute consisting of:

a chemical mixture in a ratio of about three parts potassium bicarbonate, $KHCO_3$, to about one part sodium bicarbonate, $NaHCO_3$;

a bicarbonate pill, tablet, caplet, or capsule formed in swallowable size from said chemical mixture so as to enter the human body in bicarbonate form; and hydrogen ions ($H^+$) of body acidic waste are reduced to $H_2O$ when the body stomach acid dissolves the swallowed bicarbonate pill into the blood stream where the lungs remove $CO_2$ from the bicarbonate creating hydroxyl ions ($OH^-$) which reduce ($H^+$) ions to $H_2O$, and thus convert the bicarbonates into an alkaline blood buffer for control of the body Ph.

2. A non caustic, swallowable pill in accordance with claim 1 and further comprising:

a time release coating material for said pill, tablet, caplet, or capsule.

3. A non caustic, swallowable pill in accordance with claim 2, which pill is used once a day rather than drinking about fifty ounces of alkaline water.

4. A non caustic, swallowable pill in accordance with claim 1, wherein said chemical mixture further comprises:

a balanced chemical supply of potassium bicarbonate and sodium bicarbonate minerals that relies upon the body's natural processes for producing potassium and sodium hydroxide in the blood; and said chemical supply of minerals neutralizes acid hydrogen ions ($H^+$) in body waste as the excess ($H^+$) ions in body acid become $H_2O$ by combination with said hydroxyl ($OH^-$) ions.

5. A non caustic, swallowable pill in accordance with claim 1 wherein said three parts potassium bicarbonate, $KHCO_3$, to about one part sodium bicarbonate, $NaHCO_3$ is a substitute for drinking about fifty ounces of alkaline drinking water daily, and said substitute consists of about:

580 mg of potassium bicarbonate, $KHCO_3$; and 210 mg of sodium bicarbonate, $NaHCO_3$ mixed with said specified quantity of potassium bicarbonate, $KHCO_3$.

6. A non caustic, swallowable pill in accordance with claim 5 for neutralizing body acid when consumed, and said pill is further characterized in that:

said bicarbonates are activated to alkaline within the users body by the lungs withdrawal of carbon dioxide from the bicarbonate leaving alkaline potassium hydroxide and sodium hydroxide in the blood for control of the Ph of the body.

7. A dry oral intake chemical intended for use over prolonged duration for neutralizing body acid when consumed, said chemical said chemical further characterized by consisting of:

a mixture of dry potassium bicarbonate ($KHCO_3$) and a lesser amount of dry sodium bicarbonate ($NaHCO_3$), which chemical is consumed in bicarbonate form into the body, where it is activated to alkaline by the lungs withdrawal of carbon dioxide from the consumer's body fluids as the body naturally produces hydroxides (KOH and NaOH) with hydroxyl ions ($OH^-$);

further characterized by consisting of about 75% potassium bicarbonate mixed in a chemical compound with about 25% sodium bicarbonate by weight in bicarbonate form as consumed in dry bicarbonate form into the human body; and which mixture provides a substitute for the consumer's act of drinking about fifty ounces of alkaline drinking water daily.

8. A non-liquid human consumable substitute in pill, caplet, tablet or capsule form, said pill consisting of:

about 580 mg of potassium bicarbonate, $KHCO_3$, and about 210 mg of sodium bicarbonate, $NaHCO_3$ in bicarbonate form as consumed into the human body.

9. A human consumable substitute in accordance with claim 8 and further comprising:

a time release form for said pill, caplet, tablet or capsule.

* * * * *